US011701066B2

(12) United States Patent
Yan et al.

(10) Patent No.: US 11,701,066 B2
(45) Date of Patent: Jul. 18, 2023

(54) DEVICE AND METHOD FOR DETECTING CLINICALLY IMPORTANT OBJECTS IN MEDICAL IMAGES WITH DISTANCE-BASED DECISION STRATIFICATION

(71) Applicant: Ping An Technology (Shenzhen) Co., Ltd., Shenzhen (CN)

(72) Inventors: Ke P Yan, Bethesda, MD (US);
Zhuotun Zhu, Bethesda, MD (US);
Dakai Jin, Bethesda, MD (US);
Jinzheng Cai, Bethesda, MD (US);
Adam P Harrison, Bethesda, MD (US); Dazhou Guo, Bethesda, MD (US); Le Lu, Bethesda, MD (US)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 307 days.

(21) Appl. No.: 17/094,984

(22) Filed: Nov. 11, 2020

(65) Prior Publication Data

US 2021/0233240 A1     Jul. 29, 2021

Related U.S. Application Data

(60) Provisional application No. 62/962,281, filed on Jan. 17, 2020.

(51) Int. Cl.
*A61B 6/03* (2006.01)
*G06T 7/00* (2017.01)
(Continued)

(52) U.S. Cl.
CPC .............. *A61B 6/037* (2013.01); *A61B 6/032* (2013.01); *A61B 6/5217* (2013.01);
(Continued)

(58) Field of Classification Search
CPC .......... G06T 7/0014; G06T 7/70; G06T 9/00; G06T 11/008; G06T 2207/10081;
(Continued)

(56) References Cited

U.S. PATENT DOCUMENTS

2010/0166276 A1\* 7/2010 Dube ................... G06T 5/002
382/131
2017/0165500 A1\* 6/2017 Flynn .................. A61N 5/103
(Continued)

OTHER PUBLICATIONS

Yang, Xin, et al. "Co-trained convolutional neural networks for automated detection of prostate cancer in multi-parametric MRI." Medical image analysis 42 (2017): 212-227. (Year: 2017).\*
(Continued)

*Primary Examiner* — Vu Le
*Assistant Examiner* — Julius Chai
(74) *Attorney, Agent, or Firm* — Anova Law Group, PLLC

(57) ABSTRACT

A method for performing a computer-aided diagnosis (CAD) includes: acquiring a medical image set; generating a three-dimensional (3D) tumor distance map corresponding to the medical image set, each voxel of the tumor distance map representing a distance from the voxel to a nearest boundary of a primary tumor present in the medical image set; and performing neural-network processing of the medical image set to generate a predicted probability map to predict presence and locations of oncology significant lymph nodes (OSLNs) in the medical image set, wherein voxels in the medical image set are stratified and processed according to the tumor distance map.

20 Claims, 7 Drawing Sheets

(51) Int. Cl.
    *G06T 11/00*     (2006.01)
    *G06T 9/00*     (2006.01)
    *A61B 6/00*     (2006.01)
    *G06N 3/08*     (2023.01)
    *G16H 30/40*     (2018.01)
    *G16H 50/20*     (2018.01)
    *G06T 7/70*     (2017.01)
    *G06F 18/21*     (2023.01)
    *G06F 18/25*     (2023.01)
    *G06V 10/764*     (2022.01)
    *G06V 10/80*     (2022.01)

(52) U.S. Cl.
    CPC ............ *A61B 6/5235* (2013.01); *G06F 18/21* (2023.01); *G06F 18/251* (2023.01); *G06N 3/08* (2013.01); *G06T 7/0014* (2013.01); *G06T 7/70* (2017.01); *G06T 9/00* (2013.01); *G06T 11/008* (2013.01); *G06V 10/764* (2022.01); *G06V 10/806* (2022.01); *G16H 30/40* (2018.01); *G16H 50/20* (2018.01); *G06T 2207/10081* (2013.01); *G06T 2207/10104* (2013.01); *G06T 2207/20076* (2013.01); *G06T 2207/20084* (2013.01); *G06T 2207/30096* (2013.01); *G06V 2201/03* (2022.01)

(58) Field of Classification Search
    CPC . G06T 2207/10104; G06T 2207/20076; G06T 2207/20084; G06T 2207/30096; G16H 50/20; G16H 30/40; G06V 10/40; G06V 2201/03; A61B 6/032; A61B 6/037; A61B 6/5217; A61B 6/5235; G06K 9/6217; G06K 9/6289; G06N 3/08
    See application file for complete search history.

(56) References Cited

U.S. PATENT DOCUMENTS

2017/0209712 A1*   7/2017   Hårdemark ............... G06T 7/11
2019/0287240 A1*   9/2019   Gaire .................... G06T 7/0012

OTHER PUBLICATIONS

A. Pezeshk, S. Hamidian, N. Petrick and B. Sahiner, "3-D Convolutional Neural Networks for Automatic Detection of Pulmonary Nodules in Chest CT," in IEEE Journal of Biomedical and Health Informatics, vol. 23, No. 5, pp. 2080-2090, Sep. 2019, doi: 10.1109/JBHI.2018.2879449. (Year: 2019).*

* cited by examiner

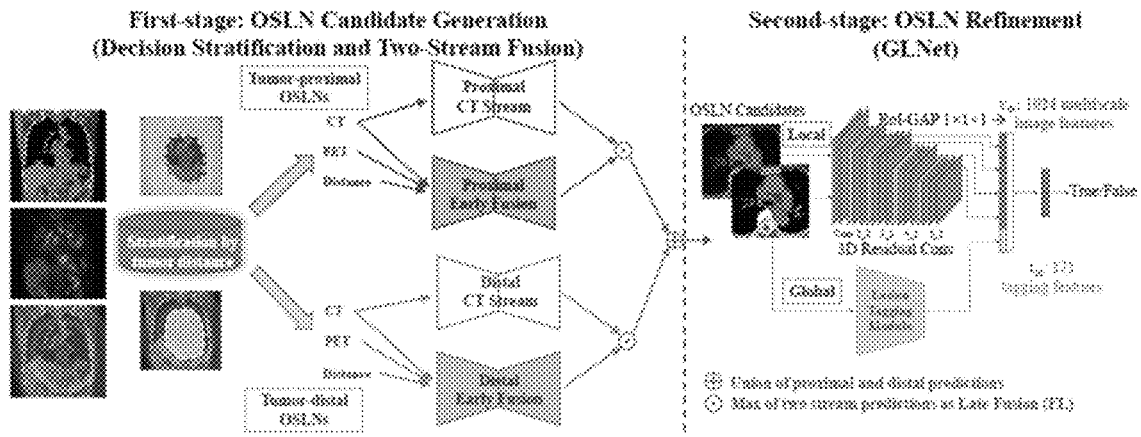

FIG. 6

S230 — Process the medical image set with a detection network containing a single encoder followed by a plurality of decoder branches, wherein the single encoder is trained to extract common OSLN features, and each decoder branch is trained to extract and output a subgroup of OSLN features
S236

Apply a plurality of distance-based gating functions to outputs of the plurality of decoder branches to generate a plurality of subgroups of distance-gated OSLN features
S237

Fuse the plurality of subgroups of distance-gated OSLN features to form the predicted probability map
S238

FIG. 7

DEVICE AND METHOD FOR DETECTING CLINICALLY IMPORTANT OBJECTS IN MEDICAL IMAGES WITH DISTANCE-BASED DECISION STRATIFICATION

CROSS-REFERENCE TO RELATED APPLICATION

This application claims the priority of U. S. Provisional Patent Application No. 62/962,281, filed on Jan. 17, 2020, the entire contents of which are incorporated herein by reference.

TECHNICAL FIELD

The present disclosure relates to the technical field of computer-aided diagnosis (CAD) and, in particular, to a device and method for computer-aided diagnosis (CAD) for detecting clinically important objects in medical images with distance-based decision stratification.

BACKGROUND

Measuring sizes and status of certain anatomical structures, such as lymph nodes (LNs) in oncology images, are important clinical tasks, usually used to monitor cancer diagnosis and treatment responses and to identify treatment areas for radiotherapy. According to the Revised Response Evaluation Criteria in Solid Tumors (RECIST) guideline, only enlarged LNs with a short axis more than 10-15 mm in computed tomography (CT) images should be considered as abnormal. Such enlarged LNs have been the only focus, so far, of LN segmentation and detection works. However, in cancer treatment, besides the primary tumor, all metastasis-suspicious LNs are required to be treated. This includes the enlarged LNs, as well as smaller ones that are associated with a high positron emission tomography (PET) signal or any metastasis signs in CT. This larger category is regarded as oncology significant lymph nodes (OSLNs). Metastasis suspicious LNs are also known as lymph node gross tumor volumes (GTV_LNs). Identifying the OSLNs (or GTV_LNs) and assessing their spatial relationship and causality with the primary tumor is a key requirement for a desirable cancer treatment outcome. Identifying OSLNs can be a daunting and time-consuming task, even for experienced radiation oncologists. It requires using high-level sophisticated reasoning protocols and faces strong uncertainty and subjectivity with high interobserver variability. The task on OSLNs detection is challenging for at least these reasons: (1) finding OSLNs is often performed using radiotherapy CT (RTCT), which, unlike diagnostic CT, is not contrast-enhanced; (2) OSLNs exhibit low contrast with surrounding tissues and can be easily confused with other anatomical structures, e.g., vessels and muscles, due to shape and appearance ambiguity; (3) The size and shape of OSLNs can vary considerably, and OSLNs are often scatteredly distributed at small size in a large spatial range of anatomy locations.

FIG. 1A and FIG. 1B illustrate the differences in appearance and size distribution between enlarged LNs and the larger category of OSLNs. The white dashed lines in FIG. 1A mark the contours of the LNs. The top panels of FIG. 1A show three examples of enlarged LNs in contrast-enhanced CT. The bottom panels of FIG. 1A show three instances of OSLNs in non-contrast RTCT. FIG. 1B shows LN volume distributions for enlarged LNs from a public dataset and OSLNs from a radiotherapy dataset. As shown in FIG. 1B, OSLNs have higher frequencies at smaller sizes, challenging their detection. While many previous works proposed automatic detection systems for enlarged LNs in contrast-enhanced CT, no work, as of yet, has focused on OSLN detection on non-contrast RTCT. Given the considerable differences between enlarged LNs and OSLNs, further innovation is required for robust and clinically useful OSLN detection.

SUMMARY

In one aspect of the present disclosure, a method for performing a computer-aided diagnosis (CAD) is provided. The method includes: acquiring a medical image set; generating a three-dimensional (3D) tumor distance map corresponding to the medical image set, each voxel of the tumor distance map representing a distance from the voxel to a nearest boundary of a primary tumor present in the medical image set; and performing neural-network processing of the medical image set to generate a predicted probability map to predict presence and locations of oncology significant lymph nodes (OSLNs) in the medical image set, wherein voxels in the medical image set are stratified and processed according to the tumor distance map.

According to certain embodiments of the CAD method, the medical image set includes a 3D non-contrast computer tomography (CT) image and a 3D positron emission tomography (PET) image registered to the CT image; and performing neural-network processing of the medical image set includes: dividing voxels in each of the CT image and the PET image into tumor-proximal voxels and tumor-distal voxels according to the tumor distance map and a distance threshold; processing the CT image with a first sub-network trained on CT images with corresponding ground-truth maps to generate a first prediction map based on the tumor-proximal voxels and a second prediction map based on the tumor-distal voxels; processing the CT image, the PET image, and the tumor distance map with a second sub-network jointly trained on CT images, PET images, tumor distance maps, and corresponding ground-truth maps to generate a third prediction map based on the tumor-proximal voxels and a fourth prediction map based on the tumor-distal voxels; and performing a fusion operation on the first, second, third and fourth prediction maps to generate a fused prediction map.

According to certain embodiments of the CAD method, the fusion operation includes: performing an element-wise maximum operation on the first and third prediction maps to generate a fifth prediction map; performing an element-wise maximum operation on the second and fourth prediction maps to generate a sixth prediction map; and performing a union operation on the fifth and sixth prediction maps to generate the fused prediction map.

According to certain embodiments of the CAD method, performing neural-network processing of the medical data set further includes: applying a second-stage neural-network processing on the fused prediction map to generate the predicted probability map.

According to certain embodiments of the CAD method, applying the second-stage neural-network processing on the fused prediction map includes: applying a threshold to the fused prediction map to generate a binary prediction map; based on the binary prediction map, generating OSLN candidates, each OSLN candidate corresponding to an image patch of the binary prediction map; for each OSLN candidate: processing the corresponding image patch with a local feature extractor to generate a first feature vector corresponding to local features of the OSLN candidate; processing the OSLN candidate with a global feature extractor to generate a second feature vector corresponding to complementary features that distinguish true OSLNs from false ones; concatenating the first feature vector with the second feature vector to generate a combined feature vector; and passing the combined feature vector through a fully connected neural network (CNN) layer to generate a final OSLN classification score for the OSLN candidate.

According to certain embodiments of the CAD method, the local feature extractor includes a multi-scale 3D CNN with a 3D region of interest (ROI)-global average pulling (GAP) layer.

According to certain embodiments of the CAD method, the global feature extractor includes a lesion tagging module pre-trained on radiology reports including a variety of tissue types.

According to certain embodiments of the CAD method, performing neural-network processing of the medical image set includes: processing the medical image set with a detection network containing a single encoder followed by a plurality of decoder branches, wherein the single encoder is trained to extract common OSLN features, and each decoder branch is trained to extract and output a subgroup of OSLN features; applying a plurality of distance-based gating functions to outputs of the plurality of decoder branches to generate a plurality of subgroups of distance-gated OSLN features, wherein each distance-based gating function applies tumor-distance dependent OSLN sample weights to the output of a corresponding decoder branch according to the tumor distance map to generate one subgroup of distance-gated OSLN features; and fusing the plurality of subgroups of distance-gated OSLN features to form the predicted probability map.

According to certain embodiments of the CAD method, the medical image set includes a 3D non-contrast CT image and a 3D PET image registered to the CT image; and performing neural-network processing of the medical image set includes an early fusion of the CT image, the PET image, and the tumor distance map.

According to certain embodiments of the CAD method, the detection network contains two decoder branches including a first decoder branch and a second decoder branch; and the distance-based gating functions include a first binary distance gating function configured to pass tumor-proximal features and a second binary distance gating function configured to pass tumor-distal features.

According to certain embodiments of the CAD method, the distance-based gating functions are soft gating functions having OSLN sample weights linearly dependent on distances to the primary tumor.

In another aspect of the present disclosure, a device for performing computer-aided diagnosis (CAD) is provided. The device includes: a memory, storing computer-executable instructions; and a processor, coupled with the memory and, when the computer-executable instructions being executed, configured to: acquire a medical image set; generate a three-dimensional (3D) tumor distance map corresponding to the medical image set, each voxel of the tumor distance map representing a distance from the voxel to a nearest boundary of a primary tumor present in the medical image set; and perform neural-network processing of the medical image set to generate a predicted probability map to predict presence and locations of oncology significant lymph nodes (OSLNs) in the medical image set, wherein voxels in the medical image set are stratified and processed according to the tumor distance map.

According to certain embodiments of the device, the medical image set includes a 3D non-contrast computer tomography (CT) image and a 3D positron emission tomography (PET) image registered to the CT image; and the processor is further configured to: divide voxels in each of the CT image and the PET image into tumor-proximal voxels and tumor-distal voxels according to the tumor distance map and a distance threshold; process the CT image with a first sub-network trained on CT images with corresponding ground-truth maps to generate a first prediction map based on the tumor-proximal voxels and a second prediction map based on the tumor-distal voxels; process the CT image, the PET image, and the tumor distance map with a second sub-network jointly trained on CT images, PET images, tumor distance maps, and corresponding ground-truth maps to generate a third prediction map based on the tumor-proximal voxels and a fourth prediction map based on the tumor-distal voxels; and perform a fusion operation on the first, second, third and fourth prediction maps to generate a fused prediction map.

According to certain embodiments of the device, the processor is further configured to: perform an element-wise maximum operation on the first and third prediction maps to generate a fifth prediction map; perform an element-wise maximum operation on the second and fourth prediction maps to generate a sixth prediction map; and perform a union operation on the fifth and sixth prediction maps to generate the fused prediction map.

According to certain embodiments of the device, the processor is further configured to: apply a second-stage neural-network processing on the fused prediction map to generate the predicted probability map.

According to certain embodiments of the device, the processor is further configured to: process the medical image set with a detection network containing a single encoder followed by a plurality of decoder branches, wherein the single encoder is trained to extract common OSLN features, and each decoder branch is trained to extract and output a subgroup of OSLN features; apply a plurality of distance-based gating functions to outputs of the plurality of decoder branches to generate a plurality of subgroups of distance-gated OSLN features, wherein each distance-based gating function applies tumor-distance dependent OSLN sample weights to the output of a corresponding decoder branch according to the tumor distance map to generate one subgroup of distance-gated OSLN features; and fuse the plurality of subgroups of distance-gated OSLN features to form the predicted probability map.

In another aspect of the present disclosure, a non-transitory computer-readable storage medium is provided. The non-transitory computer-readable storage medium stores a plurality of instructions, wherein when the plurality of instructions are executed by a processor, cause the processor to: acquire a medical image set; generate a three-dimensional (3D) tumor distance map corresponding to the medical image set, each voxel of the tumor distance map representing a distance from the voxel to a nearest boundary of a primary tumor present in the medical image set; and perform neural-network processing of the medical image set to generate a predicted probability map to predict presence and locations of oncology significant lymph nodes (OSLNs) in the medical image set, wherein voxels in the medical image set are stratified and processed according to the tumor distance map.

According to certain embodiments of the non-transitory computer-readable storage medium, the medical image set includes a 3D non-contrast computer tomography (CT) image and a 3D positron emission tomography (PET) image registered to the CT image; and when the plurality of instructions are executed by a processor, the processor is further caused to: divide voxels in each of the CT image and the PET image into tumor-proximal voxels and tumor-distal voxels according to the tumor distance map and a distance threshold; process the CT image with a first sub-network trained on CT images with corresponding ground-truth maps to generate a first prediction map based on the tumor-proximal voxels and a second prediction map based on the tumor-distal voxels; process the CT image, the PET image, and the tumor distance map with a second sub-network jointly trained on CT images, PET images, tumor distance maps, and corresponding ground-truth maps to generate a third prediction map based on the tumor-proximal voxels and a fourth prediction map based on the tumor-distal voxels; and perform a fusion operation on the first, second, third and fourth prediction maps to generate a fused prediction map.

According to certain embodiments of the non-transitory computer-readable storage medium, when the plurality of instructions are executed by a processor, the processor is further caused to: perform an element-wise maximum operation on the first and third prediction maps to generate a fifth prediction map; perform an element-wise maximum operation on the second and fourth prediction maps to generate a sixth prediction map; and perform a union operation on the fifth and sixth prediction maps to generate the fused prediction map.

According to certain embodiments of the non-transitory computer-readable storage medium, when the plurality of instructions are executed by a processor, the processor is further caused to: process the medical image set with a detection network containing a single encoder followed by a plurality of decoder branches, wherein the single encoder is trained to extract common OSLN features, and each decoder branch is trained to extract and output a subgroup of OSLN features; apply a plurality of distance-based gating functions to outputs of the plurality of decoder branches to generate a plurality of subgroups of distance-gated OSLN features, wherein each distance-based gating function applies tumor-distance dependent OSLN sample weights to the output of a corresponding decoder branch according to the tumor distance map to generate one subgroup of distance-gated OSLN features; and fuse the plurality of subgroups of distance-gated OSLN features to form the predicted probability map.

BRIEF DESCRIPTION OF THE DRAWINGS

In order to more clearly illustrate the technical solutions according to the embodiments of the present disclosure, the drawings used in the description of the embodiments will be briefly described below. The drawings in the following description are only some embodiments of the present disclosure. Other drawings may be obtained by those of ordinary skill in the art based on these drawings.

FIG. 6 illustrates an example of implementing the CAD method according to certain embodiments as shown in FIG. 4 and FIG. 5;

FIG. 7 illustrates an implementation process of Step S230 in the method shown in FIG. 4 according to certain embodiments of the present disclosure;

DETAILED DESCRIPTION

Figure 1A:
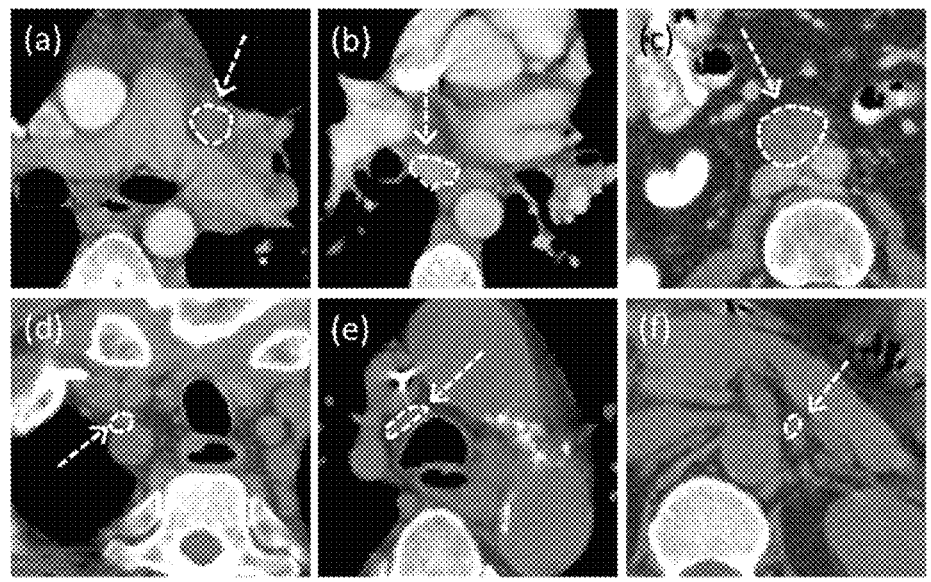
FIG. 1A illustrates examples of enlarged lymph nodes (LNs) in contrast-enhanced CT and oncology significant lymph nodes (OSLNs) in non-contrast RTCT.
Figure 1B:
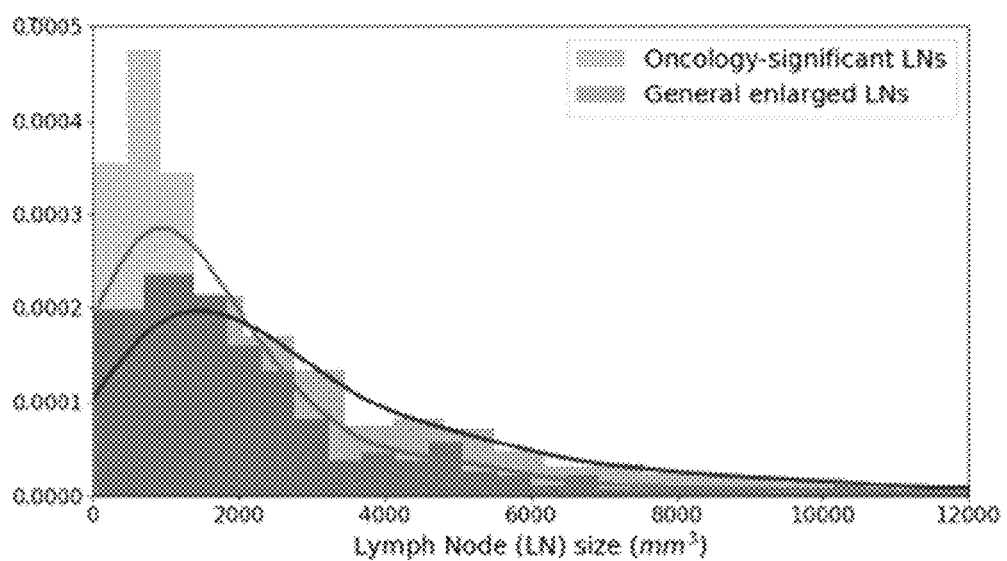
FIG. 1B illustrates LN volume distributions for enlarged LNs from a public dataset and OSLNs from a radiotherapy dataset.

The technical solutions according to the embodiments of the present disclosure are described in the following with reference to the accompanying drawings. The described embodiments are only part of the embodiments of the present disclosure, but not all the embodiments. All other embodiments obtained by a person of ordinary skill in the art based on the embodiments of the present disclosure without creative efforts are within the scope of the present disclosure.

The present disclosure provides a device and method for computer-aided diagnosis (CAD) based on medical images. The CAD device and method provided in the present disclosure may be applied in automatically detecting, identifying. and characterizing clinically important objects, such as oncology significant lymph nodes (OSLNs) or lymph node gross tumor volumes (GTV_LNs), in medical images.

There are two popular approaches for generic lesion detection: end-to-end and two-stage methods. End-to-end methods have been extensively applied to the universal lesion detection task in the largest general lesion dataset currently available, i.e., DeepLesion, and achieved encouraging performance. Notably, a multi-task universal lesion analysis network (MULAN) so far achieves the best detection accuracy using a 3D feature fusion strategy and Mask R-CNN architecture.

In contrast, two-stage methods explicitly divide the detection task into candidate generation and FP reduction steps. The first step generates the initial candidates at a high recall and FP rate and the second step focuses on reducing the FP rate (especially the difficult ones) while maintaining a sufficient high recall. It decouples the task into easier sub-tasks and allows for the optimal design of each sub-task, which has shown to be more effective in problems like lung nodule and brain lacune detection as compared to the one-stage method. According to certain embodiments, the present disclosure adopts the two-stage strategy for oncology significant lymph node (OSLN) detection to effectively incorporate different features, i.e., PET imaging, tumor distance map, and high-semantic lesion attributes, into each stage.

Previous works focus only on enlarged LN detection and segmentation in contrast-enhanced CT. Conventional statistical learning approaches employ hand-crafted image features, such as shape, spatial priors, Haar filters, and volumetric directional difference filters, to capture LN appearance and location. More recent deep learning methods achieve better performance. Certain recent works apply the FCN or Mask R-CNN to directly segment LNs. Certain other recent works adopted a 2.5D patch-based convolutional neural network (CNN) with random view aggregation to classify LNs given all LN candidates already detected, and achieves SOTA classification accuracy for enlarged LNs. By contrast, according to certain embodiments, the present disclosure effectively applies the local and global modules in a global-local network, termed as the GLNet.

The multi-modal imaging setup is a common and effective representation for segmenting anatomical structures in medical images. The pixel contrast and visual information in each modality may be different and complementary for many applications. In the present disclosure, according to certain embodiments, RTCT and PET have fundamentally different imaging physics, with RTCT corresponding to anatomy-based structural imaging and PET to functional imaging. Recent deep learning approaches have exploited different fusion strategies for PET/CT, e.g., early, late or chained fusion. As a 1st-stage process, according to certain embodiments, the present disclosure provides a 2-stream deep network segmentation workflow (encoding RTCT alone or combined RTCT/PET and tumor distance map, respectively) and implements a concise late probability fusion scheme. This two-stream fusion strategy may effectively generate the OSLN candidates with a high recall at a reasonable FP rate, which is desirable for the downstream 2nd-stage FP reduction.

Current clinical practices offer certain insight in how to tackle the of detecting oncology significant lymph nodes (OSLNs). For instance, physicians may condition their analysis of suspicious areas based on their distance to the primary tumor. For LNs proximal to the tumor, physicians will more readily identify them as OSLNs for the radiotherapy treatment. However, for LNs far away from the tumor, physicians are more discriminating, only including them if there are clear signs of metastasis, such as enlarged in size, increased PET signals, and/or other CT-based evidence. Hence, distance to the primary tumor plays a key role in the physician's decision making. Besides the distance, the PET modality is also highly important, as it significantly increases sensitivity. However, PET is noisy, and increased PET signals can often associate with normal physiological uptake. Moreover, PET only highlights 33% of the OSLNs.

Figure 2A:
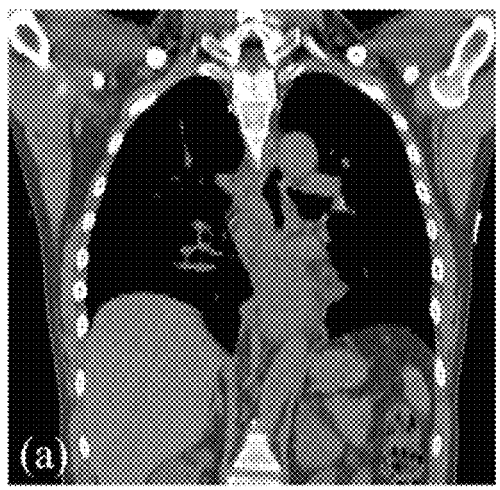
FIG. 2A illustrates a coronal view of an RTCT image for an esophageal cancer patient.
Figure 2B:
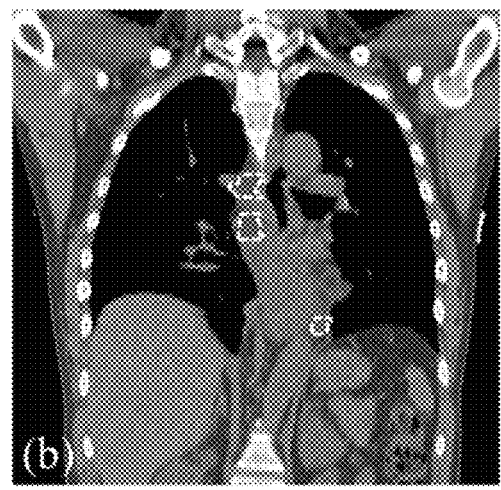
FIG. 2B illustrates a manually annotated oncology significant lymph node (OSLN) contours corresponding to the RTCT image shown in FIG. 2A.
Figure 2C:
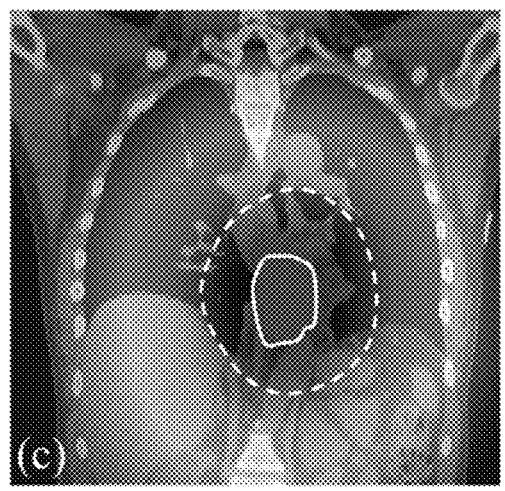
FIG. 2C illustrates a tumor distance transform map overlaid on RTCT image shown in FIG. 2A.
Figure 2D:
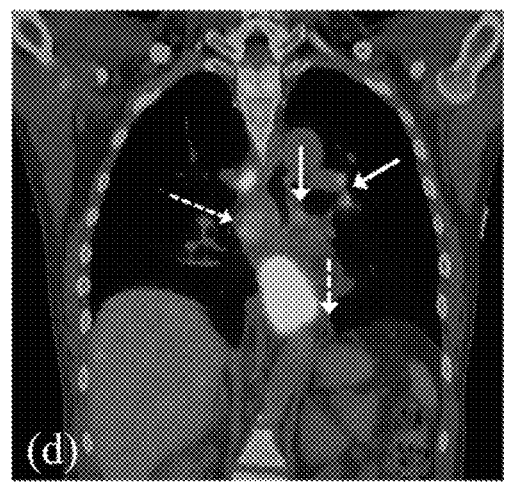
FIG. 2D shows a PET image overlaid on the RTCT image shown in FIG. 2A.

FIGS. 2A-2D illustrate an example of oncology images of an esophageal cancer patient. FIG. 2A shows a coronal view of an RTCT for the patient. FIG. 2B shows a manually annotated OSLN mask indicated by white dash-line contours. FIG. 2C shows tumor distance transform map overlaid on RTCT, where the primary tumor is indicated by a solid-line circled contour in the center and the white dash line shows an example of the tumor proximal and distal region division. FIG. 2D shows a PET image overlaid on the RTCT. The solid-line while arrows show several FP PET signals, and the dashed while arrows indicate two FN OSLNs where PET has weak or even no signals. A central bright region in PET corresponds to the primary tumor region. As demonstrated in FIG. 2D, the PET image provides key information in identifying OSLNs, which might be too difficult to detect from RTCT only. Yet, the PET also exhibits false positives (FPs) and false negatives (FNs). Based on this observation, an effective method to leverage the complementary information in RTCT and PET is crucial, but this must be done with care.

To solve the above problem, the present disclosure provides a computer-aided diagnosis (CAD) system and method that emulates and disentangles the clinical practices as described above. First, according to certain embodiments, an intuitive and effective strategy may use distance stratification to decouple the underlying OSLN distributions into two "tumor-proximal" and "tumor-distal" categories, followed by training separate networks to fit the category-specific imaging features to the task. LNs that are spatially close to the primary tumor site are more suspicious (even if they are not enlarged); whereas spatially distal OSLNs may need to be identified with both CT and PET imaging evidence. This type of decision uncertainty stratification is evident in medical diagnosis and the present disclosure provides a CAD realization of the strategy.

Second, according to certain embodiments, for each OSLN category, the present disclosure provides a 3D detection-by-segmentation framework that fuses predictions from two independent sub-networks, one trained on the RTCT imaging alone and the other learned via the early fusion (EF) of three channels of RTCT, PET, and a 3D tumor distance map. (FIG. 2C shows an example of the 3D tumor distance map.) The RTCT may depict anatomical structures, which capture intensity appearance and contextual information, serves as a good baseline diagnostic imaging modality. In contrast, the EF stream may take into account the PET's metastasis functional sensitivities as well as the tumor distance encoded in the distance transform map, which are both noisy but informative. Along with the distance stratification, this produces four predictions, which are all fused together as a late fusion (LF). The processes provided by the present disclosure may produce OSLN predictions that achieve sufficiently high sensitivities in finding OSLNs, which complements the high specificity but low sensitivity of human observers, and thus offers a clinically significant improvement in diagnostic quality since missing true OSLNs can cause oncologically critical areas to remain untreated.

Third, according to certain embodiments, the present disclosure provides a global-local network (GLNet) to further reduce the FP OSLN candidates obtained from above. The GLNet includes two modules, with each module corresponding to the global or local spatial context. For local context, a process may crop out any OSLN candidate region with certain context margins and adopt 3D residual convolutions to extract instance-wise localized deep feature maps. For a global context, a process may leverage the ontology-based medical knowledge from the large-scale NIH DeepLesion dataset via a lesion tagging module, which provides high-level semantic information such as body part and shape/texture/size attributes that cannot be easily captured from local 3D image patches. The strategy of looking at locally (i.e., the imaging space) and globally (i.e., the semantic ontology space) is essential to mimic sophisticated clinical reasoning protocols. Both the imaging texture and appearance and semantically meaningful attributes are crucial to allow the workflow to filter out FPs while keeping sensitivities high.

Further, according to certain other embodiments, the present disclosure provides a distance-based gating strategy in a multi-task framework to divide the underlying OSLN distributions into tumor-proximal and tumor-distal categories and solve them accordingly. Specifically, a multi-branch network is provided. According to certain embodiments, the multi-branch network may include a shared encoder and multiple separate decoders to detect and segment the tumor-proximal and tumor-distal OSLN, respectively. A distance-based gating function is designed to generate the corresponding OSLN sample weights for each branch. By applying the gating function at the outputs of decoders, each branch is specialized to learn the "tumor-proximal" or "tumor-distal" OSLN features that emulates the physician's diagnosis process. According to certain embodiments, an early fusion (EF) of three modalities may be used to generate an input to the model, i.e., RTCT, PET, and 3D tumor distance map. RTCT depicts anatomical structures capturing the intensity, appearance, and contextual information, while PET provides metastasis functional activities. Meanwhile, the tumor distance map further encodes the critical distance information in the network. Fusion of these three modalities together can effectively boost the OSLN identification performance.

Figure 3:
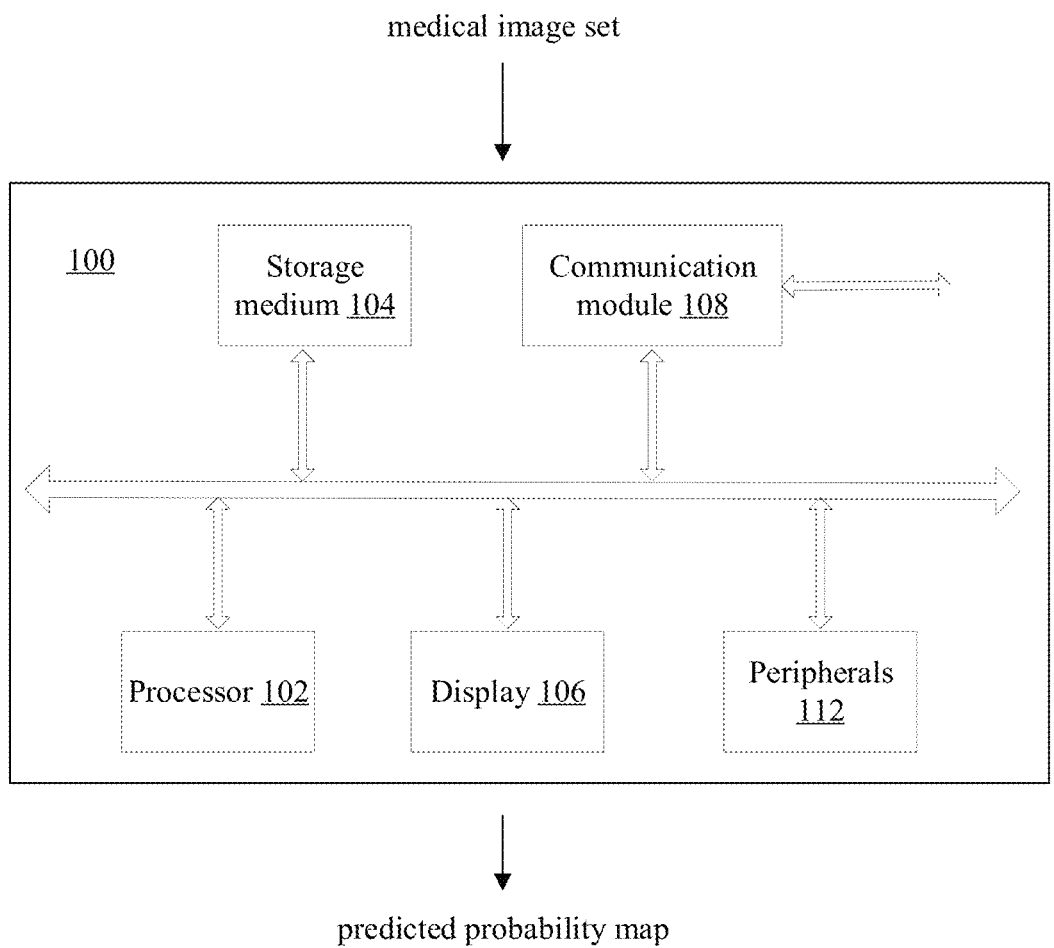
FIG. 3 illustrates a CAD device for detecting clinically important objects in medical images according to certain embodiments of the present disclosure.

FIG. 3 illustrates a CAD device 100 for detecting clinically important objects in medical images according to certain embodiments of the present disclosure. As shown in FIG. 3, the CAD device 100 may be configured to receive medical images containing anatomical structures. In certain embodiments, the received medical image may be a 3D medical image, such as a 3D radiotherapy computer-tomography (RTCT) scan image and a 3D positron emission tomography (PET) image. The medical images may be obtained from one or more imaging instrument, loaded from a memory module, or otherwise provided to the CAD device. The CAD device 100 may be configured to perform neural-network processing to identify and locate one or more clinically important objects, such as one or more OSLNs, from the medical images, and generate an output to provide detection information. In certain embodiments, the output detection result may include a predicted probability map corresponding to the input images. The value of each pixel or voxel of the predicted probability map may represent a probability of the pixel or voxel corresponding to an OSLN. Parameters of the neural network may be generated by a training process configured to receive training data containing a plurality of annotated medical images.

In some embodiments, the CAD device 100 may be a computing device including a processor 102 and a storage medium 104. The CAD device 100 may further include a display 106, a communication module 108, and additional peripheral devices 112. Certain devices may be omitted, and other devices may be included. Processor 102 may include any appropriate processor(s). In certain embodiments, processor 102 may include multiple cores for multi-thread or parallel processing. Processor 102 may execute sequences of computer program instructions to perform various processes, such as a neural network processing program. Storage medium 104 may be a non-transitory computer-readable storage medium, and may include memory modules, such as ROM, RAM, flash memory modules, and erasable and rewritable memory, and mass storages, such as CD-ROM, U-disk, and hard disk, etc. Storage medium 104 may store computer programs and instructions for implementing various processes, when executed by processor 102, cause the processor to perform various steps of the neural network processing program of a CAD method for detecting and locating anatomical abnormalities from a medical image. The communication module 108 may include network devices for establishing connections through a network. Display 106 may include any appropriate type of computer display device or electronic device display (e.g., CRT or LCD based devices, touch screens). Peripherals 112 may include additional I/O devices, such as a keyboard, a mouse, and so on. The processor 102 may be configured to execute instructions stored on the storage medium 104 and perform various operations related to the CAD method as detailed in the following descriptions.

Figure 4:
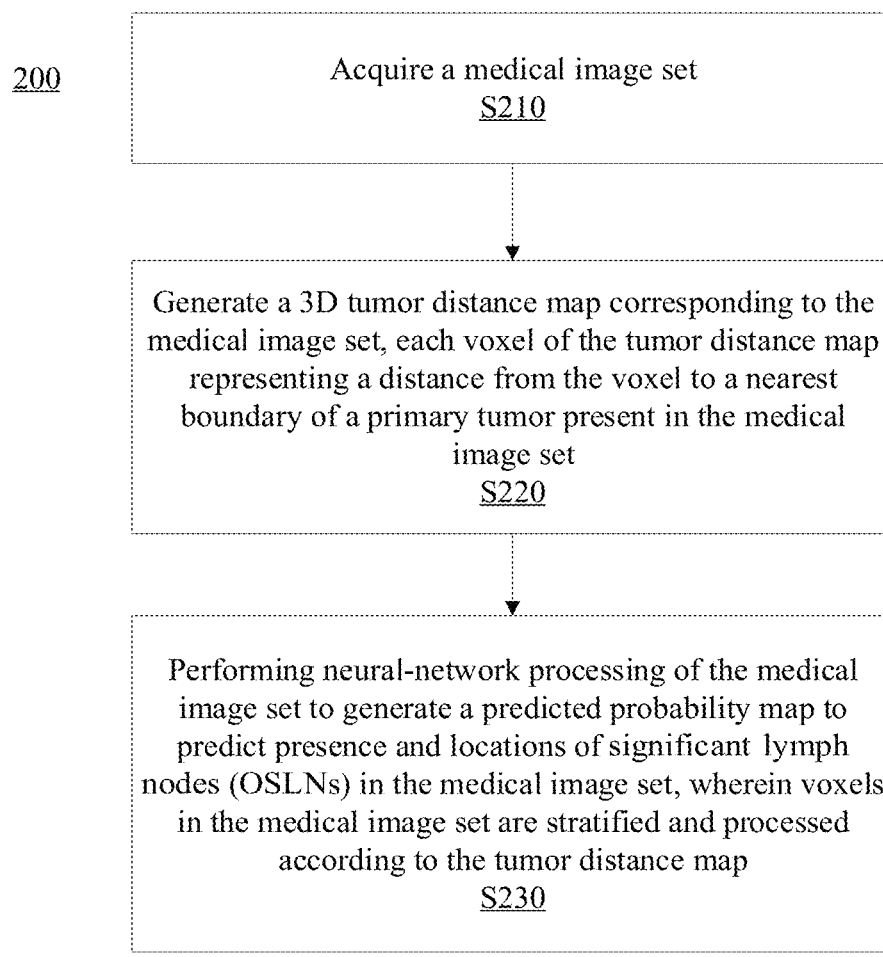
FIG. 4 illustrates a CAD method for OSLN detection from medical images according to some embodiments of the present disclosure.

FIG. 4 illustrates a CAD method 200 for OSLN detection from medical images according to some embodiments of the present disclosure. As shown in FIG. 4, the CAD OSLN detection method 200 may include the following exemplary steps.

Step S210 is to acquire a medical image set. According to certain embodiments, the medical image set may include a 3D non-contrast computer tomography (CT) image and a 3D positron emission tomography (PET) image registered to the CT image. The CT image may provide structural information of the anatomy while the PET image may supplement the structural information with functional information.

Step S220 is to generate a 3D tumor distance map corresponding to the medical image set. Each voxel of the tumor distance map may represent a distance from the voxel to a nearest boundary of a primary tumor present in the medical image set. Since the tumor distance map encodes distance information of the voxels in the medical image set, it may be used to strategy the voxels according to their distances to the primary tumor. The tumor-distance stratification information may be used to assist the detection of the OSLNs in the medical image set.

Step S230 is to perform neural-network processing of the medical image set to generate a predicted probability map to predict the presence and locations of OSLNs in the medical image set. An aspect of the neural-network processing is that the voxels in the medical image set are stratified and processed according to the tumor distance map.

Figure 5:
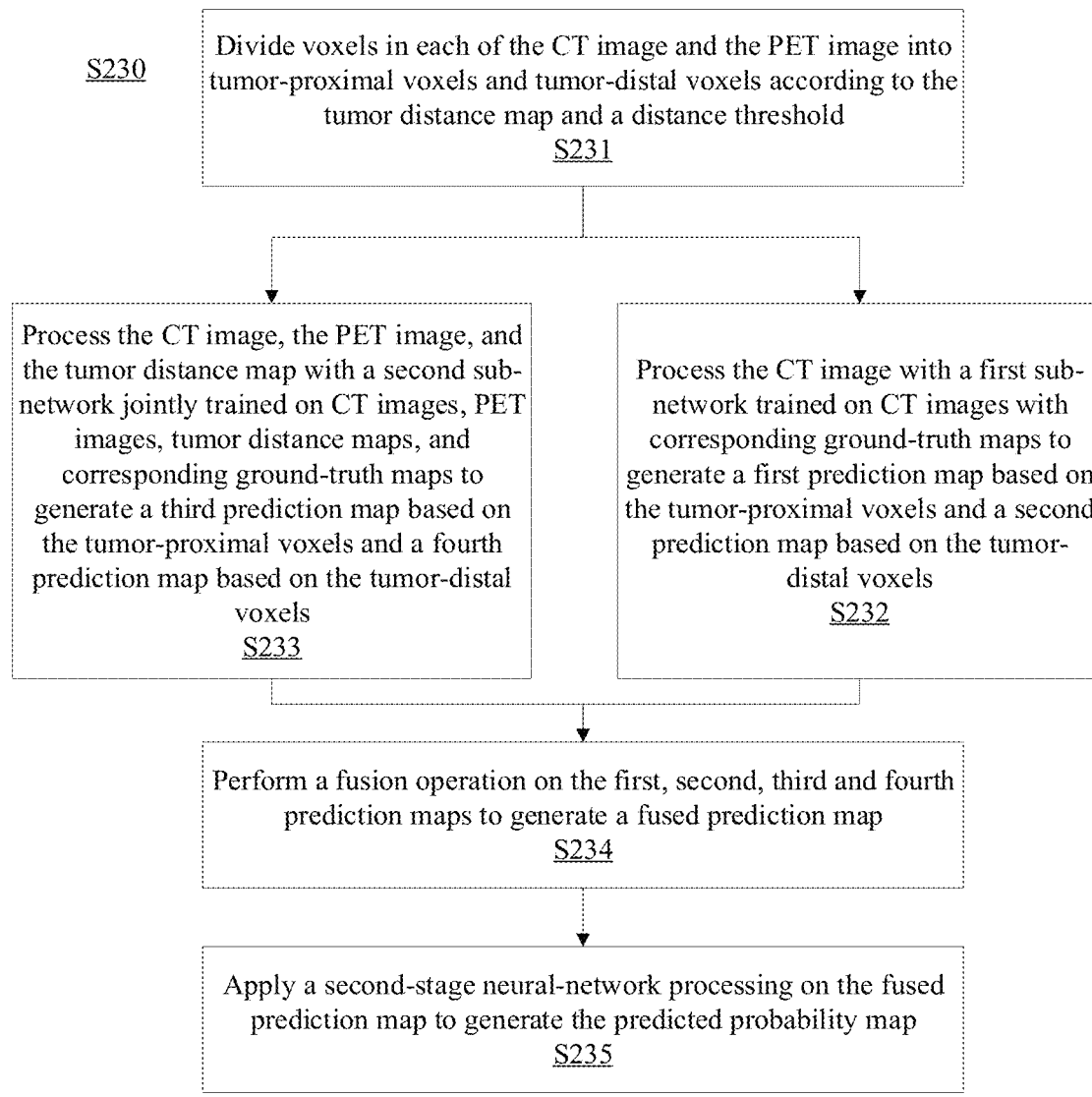
FIG. 5 illustrates an implementation of Step S230 in the method shown in FIG. 4 according to certain embodiments of the present disclosure.

FIG. 5 illustrates an implementation of Step S230 in FIG. 4 according to certain embodiments of the present disclosure. As shown in FIG. 5, according to certain embodiments, Step S230 may include the following steps.

Step S231 is to divide voxels in each of the CT image and the PET image into tumor-proximal voxels and tumor-distal voxels according to the tumor distance map and a distance threshold. Step S232 is to process the CT image with a first sub-network trained on CT images with corresponding ground-truth maps to generate a first prediction map based on the tumor-proximal voxels and a second prediction map based on the tumor-distal voxels. Step S233 may be implemented in parallel with Step S232, and include processing the CT image, the PET image, and the tumor distance map with a second sub-network jointly trained on CT images, PET images, tumor distance maps, and corresponding ground-truth maps to generate a third prediction map based on the tumor-proximal voxels and a fourth prediction map based on the tumor-distal voxels.

Step S234 is to perform a fusion operation on the first, second, third and fourth prediction maps to generate a fused prediction map. In one example, the fusion operation may include: performing an element-wise maximum operation on the first and third prediction maps to generate a fifth prediction map; performing an element-wise maximum operation on the second and fourth prediction maps to generate a sixth prediction map; and performing a union operation on the fifth and sixth prediction maps to generate the fused prediction map.

Step S235 is to apply a second-stage neural-network processing on the fused prediction map to generate the predicted probability map. In certain embodiments, the second-stage neural-network processing may include extracting both local and global features from OSLN candidates identified based on the fused prediction map. For example, the second-stage neural-network processing may include: applying a threshold to the fused prediction map to generate a binary prediction map; based on the binary prediction map, generating OSLN candidates, each OSLN candidate corresponding to an image patch of the binary prediction map; for each OSLN candidate: processing the corresponding image patch with a local feature extractor to generate a first feature vector corresponding to local features of the OSLN candidate; processing the OSLN candidate with a global feature extractor to generate a second feature vector corresponding to complementary features that distinguish true OSLNs from false ones; concatenating the first feature vector with the second feature vector to generate a combined feature vector; and passing the combined feature vector through a fully connected neural network (CNN) layer to generate a final OSLN classification score for the OSLN candidate.

FIG. 6 illustrates an example of implementing the CAD method according to certain embodiments as shown in FIG. 4 and FIG. 5. As shown in FIG. 6, a two-stage framework may be adopted. The two-stage framework may combine an OSLN candidate generation process with an FP rejection process. In the 1st-stage, the CAD method may group training-set OSLNs into two categories based on their distances to the primary tumor via distance stratification. For each category, a two-stream detection-by-segmentation network may be used to effectively incorporate and fuse the RTCT and PET images, along with a tumor distance transform map. Results from two categories are then merged together to produce the OSLN candidates. The goal of the 1st-stage is to have a set of OSLN candidates with high recall while keeping FPs to a reasonable number. In the 2nd-stage, a GLNet is designed to serve as a selective classifier to reject OSLN FP candidates (especially the difficult ones) while preserving sufficient recall. The GLNet may include a local module and a global module.

For the first stage, assuming N data samples, an image dataset may be denoted as $S=\{(X_n^{CT}, X_n^{PET}, Y_n^T, Y_n^{LN})\}_{n=1}^N$, where $X_n^{CT}, X_n^{PET}, Y_n^T$ and $Y_n^{LN}$ represent non-contrast RTCT image, registered PET image, tumor mask image, the ground truth LN segmentation mask image, respectively. Without loss of generality, in the following description, the subscript n may be dropped when appropriate. The mask $Y^T$ may be a 3D volume image with a binary value $y_i$ at each spatial location i to indicate whether the voxel $x_i$ belongs to an OSLN target. To encode tumor distance information, according to certain embodiments, the CAD method may compute a 3D signed distance transform map from the primary tumor $Y^T$. The 3D signed distance transform map may be denoted as $X^D$, where each voxel $x_i^D \in X^D$ represents a distance between this voxel to a nearest boundary of the primary tumor. $\Gamma(Y^T)$ may denote a function that computes boundary voxels of the tumor $Y^T$. The distance transform value at a voxel $x_i^D$ may be computed as $$XD(x_i^D) = \begin{cases} \min_{q \in \Gamma(Y^T)} d(x_i^D, q) & \text{if } x_i^D \notin Y^T \\ -\min_{q \in \Gamma(Y^T)} d(x_i^D, q) & \text{if } x_i^D \in Y^T \end{cases} \quad (1)$$

where $d(x_i^D, q)$ is a distance measure from $x_i^D$ to q. According to certain embodiments of the CAD method, Euclidean distance may be used for the distance measure. Further, according to certain embodiments, $X^D$ may be computed using a linear time algorithm for computing Euclidean distance transforms of binary images developed by Maurer et al. Note that $X^{CT}, X^{PET}$, and $Y^T$ are already given and $X^D$ may be pre-computed at the inference time.

According to certain embodiments, segmentation models may be denoted as a mapping: $P=f(\chi; \Theta)$, where $\chi$ is a set of inputs, which may consist of a single modality or a concatenation of multiple modalities. $\Theta$ indicates model parameters, and P denotes the predicted probability volume. Specifically, in a neural network, $\Theta$ is parameterized by the network parameters.

For distance-Based OSLN stratification based on $X^D$, according to certain embodiments, the CAD method may divide image voxels into two groups, $x_{prox}$ and $x_{dis}$, to be tumor-proximal and tumor-distal, respectively, where the tumor-proximal and tumor-distal conditions may be defined as prox=$\{i|x_i^D \leq d\}$ and dis=$\{i|x_i^D > d\}$, respectively. Accordingly, the CAD method may divide all OSLNs into two categories, and train separate segmentation models for each category. By doing this, the CAD method may break down the challenging OSLN segmentation problem into two simpler sub-problems, each of which can be more easily addressed. This allows the OSLN segmentation method to emulate the clinician decision process, where tumor-proximal LNs are more readily considered oncology-significant, whereas a more conservative process, with differing criteria, is used for tumor-distal LNs. This stratification process is illustrated by the left panel of FIG. 6. Prediction volumes generated by the tumor-proximal or tumor-distal models are denoted as $P_{prox}$ and $P_{dis}$, respectively.

For each OSLN category, the CAD method may again emulate the physician's diagnostic process by fully exploiting the complementary information within the RTCT, PET, and tumor distance map. Specifically, for each OSLN category, the CAD method may adopt a two-stream 3D segmentation workflow that fuses predictions from two independent sub-networks, one trained using the RTCT alone (CT stream), and the other trained using the three channels of RTCT, PET, and the tumor distance map jointly (early fusion stream). In this way the CAD method may generate predictions based on only structural appearance, complementing them with additional predictions incorporating PET's auxiliary functional sensitivity and the tumor distance map's location context. The prediction volumes from the RTCT and early fusion stream models may be denoted as $P_{(\cdot)}^{CT}$ and $P_{(\cdot)}^{EF}$, respectively, where the subscript may be either "prox" or "dis" for the tumor-proximal or tumor-distal categories, respectively. This process results in four separate predictions. To ensure a high recall of OSLN detection in this stage, the CAD method may apply a straightforward yet effective late fusion by taking the element-wise max and union operations of the four predictions:

$$P^{LF} = \{p_i | p_i = \text{union}\{\max\{p_{prox,i}^{CT}, p_{prox,i}^{EF}\}, \max\{p_{dis,i}^{CT}, p_{dis,i}^{EF}\}\}\}, \quad (2)$$

where $p_{(\cdot),i}^{(\cdot)} \in P_{(\cdot)}^{(\cdot)}$ and i indexes individual voxel locations. Stratifying OSLNs by tumor distance and performing two-stream fusion are both crucial for a high recall.

From the final segmentation probability $P^{LF}$, the CAD method may derive the binary segmentation mask B by thresholding, and then calculate the OSLN instance candidates as the input to the 2nd-stage.

The goal of the 2nd-stage is to reject as many FPs as possible while maintaining a sufficiently high recall. the CAD method may first aggregate all predicted OSLN instances from the 1st-stage to be $R = (C_m^{CT}, C_m^{PET}, 1_m)_{m=1}^M$ as the OSLN candidates set, where $C_m^{CT}$ and $C_m^{PET}$ denote the local RTCT and PET image patches cropped at the $m^{th}$ OSLN candidate, respectively, and the binary scalar $1_m$ is the label indicating if this instance is a true OSLN. The CAD method may formulate a classification model $q = g(C; \Phi)$, where C represents the input image patches, $\Phi$ stands for model parameters, and q denotes the predicted probability. In the following descriptions, when appropriate, the subscript m may be dropped for simplicity.

To design a highly effective OSLN classifier, especially for the difficult FPs, the CAD method may adopt a global and local network (GLNet) to leverage both local (CT appearance and PET signals) and global (spatial prior and other attributes) features.

For the local module the in GLNet, the CAD method may adopt a multi-scale 3D CNN model with a 3D ROI-GAP pooling layer to extract OSLN local features from the image patch C. Unlike the 2.5D input patch used previously, according to certain embodiments of the present disclosure, the 3D CNN may explicitly use 3D spatial information to improve classification performance. Either CT or CT+PET patches can be fed into the local model, and the 3D CNN model may evaluate both options. The features generated by each convolutional block separately pass through a 3D ROI-GAP pooling layer and a fully connected layer to form a 256-dimensional (256D) vector. The 256D vectors are then concatenated together to a multi-scale local representation for the OSLN instance. In certain embodiments, the CAD method may use 4 CNN blocks, which leads to a total of 4×256=1024-dimensional (1024D) feature vector denoted as v. The 2nd-stage process is illustrated in the right panel of FIG. 6.

For the global module of the GLNet, the CAD method may migrate ontology-based medical knowledge from the large-scale DeepLesion dataset, via a pre-trained lesion tagging module, i.e., LesaNet. Trained from radiology reports, LesaNet predicts high-level semantic lesion properties in the form of a 171-dimensional vector describing the lesion's body part, type, and attributes. This information may not be easily captured from local image patches. The CAD method may use the prediction of LesaNet on the $m^{th}$ OSLN candidates to generate a 171-dimensional feature vector $t_m$, which provides complementary information to distinguish a true OSLN from false ones. For example, one body-part attribute from the feature vector indicates whether the lesion is in the "muscle", which may be confused with OSLNs when only analyzing the small local image patch, but are easier to identify under a global context. These kinds of FP candidates can be safely rejected using the global properties. LesaNet also predicts body parts like hilum LN, subcarinal LN, peritracheal LN, and attributes like hypo-attenuation, tiny, oval, which are all relevant properties to distinguish true OSLNs from false ones. To combine the strength of local image-based features and global OSLN properties, the GLNet concatenates $v_m$ and $t_m$ and passes through a fully connected layer to generate the final OSLN classification score, as illustrated in FIG. 6.

In the following examples, various aspects of the CAD method according to FIG. 4, FIG. 5, and FIG. 6 are implemented using available training datasets. The efficacy of the CAD method is demonstrated by applying the trained lesion detector on various input images.

For datasets used, an in-house dataset was collected to evaluate the 1st-stage performance as well as the overall two-stage performance. 141 non-contrast RTCTs of anonymized esophageal cancer patients were collected. All patients were undergoing radiotherapy treatments. Radiation oncologists labeled the 3D segmentation masks of the primary tumor and all OSLNs treated by radiotherapy. In total, a non-contrast RTCT scan and a PET/CT were acquired for each of the 141 patients. The RTCT scans and a PET/CT images contain 651 OSLNs with voxel-wise labels are in the mediastinum or upper abdomen regions. This dataset represents the largest annotated OSLN dataset in the chest and abdominal region to-date. The PET images were registered to the RTCT using an image registration method. For evaluation, the annotated 141 patients were randomly split into 84 for training, 23 for validation, and 34 for testing. In certain experiments, the RTCT and PET images were resampled to produce a consistent spatial resolution of 1×1×2.5 mm. For data preprocessing, Hounsfield unit values of the RTCT were truncated to be within a range of [−200, 300]. The mean and standard deviation values of PET images were also calculated across the entire training set. All PET images were then normalized with the mean and standard deviation values.

In the first stage, for training the OSLN detection-by-segmentation network, sub-volumes of 96×96×64 are cropped from the 3D images of RTCT, registered PET, and the tumor-LN distance map. For the distance stratification, a distance threshold of d=70 mm is set to divide OSLN instances into tumor-proximal and tumor-distal sub-groups as suggested by physicians. For data augmentation, straightforward and effective augmentations on training patches are used, i.e., rotation (90°, 180°, and 270°) with a probability of 0.5 and flips in the axial view with a probability of 0.25. Any popular segmentation network may be used as the 1st-stage backbone, and in the results shown in the present disclosure, standard 3D UNet is used as it gives the best performance in the network backbone ablation study. Models are trained on two NVIDIA Quadro RTX 6000 GPUs with a batch size of 8 for 50 epochs. The RAdam optimizer with a learning rate of 0.0001 is used with a momentum of 0.9 and a weight decay of 0.0005. For testing, a computationally efficient way to inference is used, i.e., sub-volumes of 224×224×64 are cropped along the vertical axis with the horizontal center the same as the center of lung masks. These sub-volume predictions are aggregated to obtain the final OSLN segmentation results.

In the 2nd-stage, to train the local module of GLNet, the input images are generated by cropping a 48×48×32 sub-volume centered around each predicted OSLN candidate from the 1st-stage. If the size of the predicted OSLN is larger than 48×48×32, the sub-volume is resized so that it contains at least an 8-voxel margin of the background along each dimension to ensure sufficient background context. The bounding boxes (bbox) for the 3D ROI-GAP pooling layer are generated by randomly jittering the bbox around the predicted OSLN with a 3-voxel range in each dimension. For the global module GLNet, the publicly available LesaNet [36] pre-trained on the DeepLesion dataset is used. The input of LesaNet is a 120×120 2D CT image patch around the OSLN candidate. The overall GLNet is trained using Adam optimizer with a learning rate of 0.0001 and a batch size of 32 for 10 epochs.

For evaluation metrics, the hit, i.e., the correct detection, is used as criteria for OSLN detection when using the segmentation results. For an OSLN prediction from the 1st-stage, if it overlaps with any ground-truth OSLN, it is treated as a hit provided that its estimated radius is similar to the radius of the ground-truth OSLN. After confirming with the physicians, a predicted radius must be within a factor of [0.5, 1.5] to the ground-truth radius.

The performance of the 1st-stage is assessed by reporting the recall at a range of desired precision points. Note that the goal of the 1st-stage is to achieve a high recall (even with quite a few FPs) so that the 2nd-stage has a high upper-bound recall to work with while it filters out FPs. The mean recall (mRecall) is reported at a precision range of [0.10, 0.20] to reflect the model performance. The recall is also reported at a precision of 0.15, which is the operating point chosen to generate inputs for the 2nd-stage. This operating point is chosen after confirming with a radiation oncologist. Both the recall and precision are macro-averaged across patients.

To evaluate both the complete workflow (1st+2nd-stage), the free-response operating characteristic (FROC) is computed, which measures the recall against different numbers of FPs allowed per patient. The CAD method may report the average recall (mFROC) at 2, 3, 4, 6 FPs per patient study. Besides the mFROC, the CAD method may also report the best F1 score a model can achieve.

A first-stage ablation study is performed to evaluate the first stage of the CAD method. Different segmentation backbones are evaluated for the OSLN candidate generation, i.e., standard UNet, UNet with squeeze-and-excitation (SE) block, HRNet, and PSNN. As shown in Table 1, the standard 3D UNet consistently outperforms other backbones. For PSNN, it may have difficulty handling this challenging task (dealing with small objects) due to its simplistic "up-sampling" decoders. For the HR-Net, due to its memory-hungry computations, the high-resolution features are added after two pooling layers, which is undesired for segmenting OSLNs. The attention module from the SE block does not help with this segmentation task either.

TABLE 1

Ablation study on the validation set: ablation study of different backbones for the CT and early fusion streams

| Backbone | Recall@ 0.15 | | mRecall@ 0.10-0.20 | |
| --- | --- | --- | --- | --- |
| | CT | EF | CT | EF |
| 3D-UNet | 0.736 | 0.732 | 0.762 | 0.722 |
| SE-UNet | 0.686 | 0.705 | 0.693 | 0.705 |
| HRNet | 0.524 | 0.656 | 0.538 | 0.638 |
| PSNN | 0.709 | 0.574 | 0.714 | 0.592 |

The effectiveness of the distance stratification method is validated under different settings. As shown in Table 2, among all settings, i.e., CT, early fusion (EF), and late fusion (LF), the distance stratification consistently improves recall@0.15 by 4%-5%. Similar improvements are seen for mRecall@0.1-0.2. These results strongly support the use of distance stratification, which is shown to be effective under different input settings.

Table 2 also reveals the importance of using and fusing different streams. As shown in Table 2, the CT stream and the EF stream achieve similar performance to each other, regardless of whether distance stratification is used or not. However, when the two streams are combined together using LF, marked improvements are observed. For example, the recall@0.15 gains 4%-5%, and the mRecall@0.1-0.2 shows similar improvements. These quantitative results validate the effectiveness of the proposed distance stratification and the two-stream network fusion.

TABLE 2

Ablation study on the validation set: 3D UNet performance with and without distance stratification. All three settings, CT, EF, and LF, are tested

| | Recall@ 0.15 | | mRecall@ 10-0.20 | |
| --- | --- | --- | --- | --- |
| Input | w/ | w/o | w/ | w/o |
| LF | 0.828 | 0.786 | 0.817 | 0.732 |
| EF | 0.788 | 0.732 | 0.760 | 0.722 |
| CT | 0.772 | 0.736 | 0.772 | 0.762 |

A second-stage ablation study is performed to evaluate the second stage of the CAD method. To gauge the impact of the 2nd-stage, the OSLN detection accuracy is directly evaluated using the 1st-stage alone. Specifically, the detection score of each OSLN instance is determined by averaging the segmentation probability for every voxel within the segmentation mask. All "1st-stage only" results in Table 3 are marked by "#". Focusing first on the LF setting, when using the 1st-stage alone it provides 0.441 F1 and 0.478 mFROC. When adding a second-stage classifier only accepting CT as input, the F1 scores and mFROC are improved to 0.513 and 0.576, respectively. Providing the PET image and global tags to the 2nd-stage classifier boosts performance even further to 0.552 and 0.645 for F1 scores and mFROC, respectively. These are clinically impactful gains. Finally, regardless of the 1st-stage setting (LF, EF, or CT), the 2nd-stage classifier provides clear improvement. This proves the versatility and strength of the workflow.

To show the necessity of both the local and global GLNet modules, purely local and purely global 2nd-stage classification performance are also evaluated. As shown in Table 3, regardless of which 1st-stage setting is used, a purely local 2nd-stage (e.g., last 2nd and 3rd rows) outperforms a purely global 2nd-stage (e.g., last 4th row). This indicates that the high-level semantic features migrated from the general lesion tagging model, i.e., LesaNet, are less effective than the local OSLN features extracted from CT or CT+PET. However, when combining the global tags with the local patches using the proposed GLNet, mFROC performance is increased from 0.594 to 0.645 (when using the LF 1st-stage setting). This demonstrates that both local and global features contribute to the ultimate performance. These observations are also valid when using the CT or EF settings for the 1st-stage.

TABLE 3

Performance comparison of different methods on the testing set. The "1st-Stage Setting" column denotes which setting is used to generate OSLN candidates. "#" means direct evaluation based on 1st-stage instance-wise segmentation scores. The "2nd-Stage Inputs" column indicates which inputs are provided to the 2nd-stage classifier. Boldface denotes the chosen 2nd-stage classifier, evaluated across different 1st-stage settings. The results are also compared against previous state-of-the-arts, the convolutional neural networks and random view aggregation and the end-to-end MULAN system

| 1st-Stage Setting | 2nd-Stage Inputs | | | Evaluation Metrics | |
|---|---|---|---|---|---|
| | CT | PET | Tag | F1 | mFROC |
| CT # | Not Applied | | | 0.407 | 0.431 |
| EF # | | | | 0.370 | 0.395 |
| LF # | | | | 0.441 | 0.478 |
| CT | ✓ | | | 0.220 | 0.067 |
| CT | | | ✓ | 0.380 | 0.408 |
| CT | ✓ | | | 0.421 | 0.449 |
| CT | ✓ | ✓ | | 0.450 | 0.491 |
| CT (GLNet) | ✓ | ✓ | ✓ | 0.513 | 0.563 |
| EF (CNN-RVA) | ✓ | | | 0.225 | 0.092 |
| EF | | | ✓ | 0.397 | 0.444 |
| EF | ✓ | | | 0.423 | 0.473 |
| EF | ✓ | ✓ | | 0.469 | 0.518 |
| EF (GLNet) | ✓ | ✓ | ✓ | 0.507 | 0.572 |
| LF (CNN-RVA) | ✓ | | | 0.257 | 0.143 |
| LF | | | ✓ | 0.471 | 0.531 |
| LF | ✓ | | | 0.513 | 0.576 |
| LF | ✓ | ✓ | | 0.526 | 0.594 |
| LF (GLNet) | ✓ | ✓ | ✓ | 0.552 | 0.645 |

| End-to-End Method | Inputs | | | Evaluation Metrics | |
|---|---|---|---|---|---|
| | CT | PET | Tag | F1 | mFROC |
| MULAN | ✓ | ✓ | ✓ | 0.436 | 0.475 |
| MULAN | ✓ | | ✓ | 0.335 | 0.348 |

Table 3 also compares the proposed two-stage OSLN detection method with two state-of-the-art methods, i.e., the multi-task universal lesion analysis network (MULAN) (achieves the best general lesion detection results in the DeepLesion dataset) and a 2.5D CNN method for classifying enlarged LNs (achieves the best 2nd-stage LN classification results in the enlarged LN dataset). The MULAN is retained using both CT and CT+PET as inputs on the radiotherapy dataset. The tagging information is naturally incorporated in MULAN regardless of input channels. Several conclusions can be drawn. First, MULAN's results, based on the CT+PET input (0.475 mFROC), are better than those based on the CT alone (0.348 mFROC), which again demonstrates the importance of PET imaging in the OSLN detecting task, even when using a single end-to-end trained model. Second, MULAN's best performance is just comparable with the best 1st-stage-only results, i.e., (LF#). This demonstrates the effectiveness of the 1st-stage with distance stratification and the two-stream network fusion. Third, the complete pipeline of the CAD method provided in the present disclosure, regardless of the 1st-stage settings, significantly outperforms the best MULAN results, e.g., CT (GLNet) achieves an mFROC score of 0.563 as compared to 0.475 from MULAN, whereas LF (GLNet) further boosts the mFROC to 0.645. This is a 22% improvement and highlights the advantages of the two-stage method, which is tailored to achieve maximum performance gain on the challenging and unique OSLN problem.

Similar to the 2nd-stage, the 2.5D CNN method is designed to classify LN candidates, but it was characterized only on enlarged LN candidates using contrast-enhanced CT. It is trained using the non-contrast CT local patches under different 1st-stage settings, i.e., CT, EF, and LF. Note that it has the worst performance among all 2nd-stage classifiers, with a best mFROC of only 0.143. This large performance degradation, particularly compared to the CT-only 2nd-stage classifier, is probably due to its 2.5D input setup and the missing of PET information. Although the 2.5D inputs and 3 orthogonal views is efficient for enlarged LN classification, this pseudo-3D analysis cannot fully leverage the 3D information that seems important to differentiate OSLNs from the background.

As discussed above and as illustrated in FIG. 4, FIG. 5, and FIG. 6, the present disclosure provides a CAD method and device using a two-stage approach to automatically detect and segment oncology significant lymph nodes (OSLNs) from non-contrast CT and PET, which has not been previously studied as a computational task. In the 1st-stage, the CAD method includes a divide-and-conquer distance stratification method by dividing OSLNs into tumor-proximal and tumor-distal categories; followed by training separate detection-by-segmentation networks to learn the category-specific features aimed to decouple this challenging task into two easier ones. In the 2nd-stage, the CAD method includes the GLNet to further reduce the false positives from the 1st-stage, by combining local appearance features from CT/PET patches and global semantic information migrated from a general lesion-characteristics-tagging model. The CAD method provided by the present disclosure is evaluated on the largest OSLN dataset of 141 esophageal cancer patients. The provided CAD method significantly improves the recall from 45% to 67% at the 3 false-positive rates per patient as compared to previous state-of-the-art methods. Thus, the CAD method and device according to the present disclosure represent an important step forward toward OSLNs detection and segmentation.

According to certain other embodiments, the stratification and processing of the image voxels according to the tumor distance map may be implemented using a branched network. FIG. 7 illustrates an implementation process of Step S230 according to certain embodiments. As shown in FIG. 7, Step S230 may include the following steps.

Step S236 is to process the medical image set with a detection network containing a single encoder followed by a plurality of decoder branches. For example, the single encoder may be trained to extract common OSLN features, and each decoder branch may be trained to extract and output a subgroup of OSLN features.

Step S237 is to apply a plurality of distance-based gating functions to outputs of the plurality of decoder branches to generate a plurality of subgroups of distance-gated OSLN features. For example, each distance-based gating function may apply tumor-distance dependent OSLN sample weights to the output of a corresponding decoder branch according to the tumor distance map to generate one subgroup of distance-gated OSLN features. In certain embodiments, the detection network may contain two decoder branches including a first decoder branch and a second decoder branch. The distance-based gating functions include a first binary distance gating function configured to pass tumor-proximal features and a second binary distance gating function configured to pass tumor-distal features. According to certain other embodiments, the distance-based gating functions may be soft gating functions having OSLN sample weights linearly dependent on distances to the primary tumor.

Step S238 is to fuse the plurality of subgroups of distance-gated OSLN features to form the predicted probability map. Thus, both tumor-proximal features tumor-distal features are taken into account.

Figure 8:
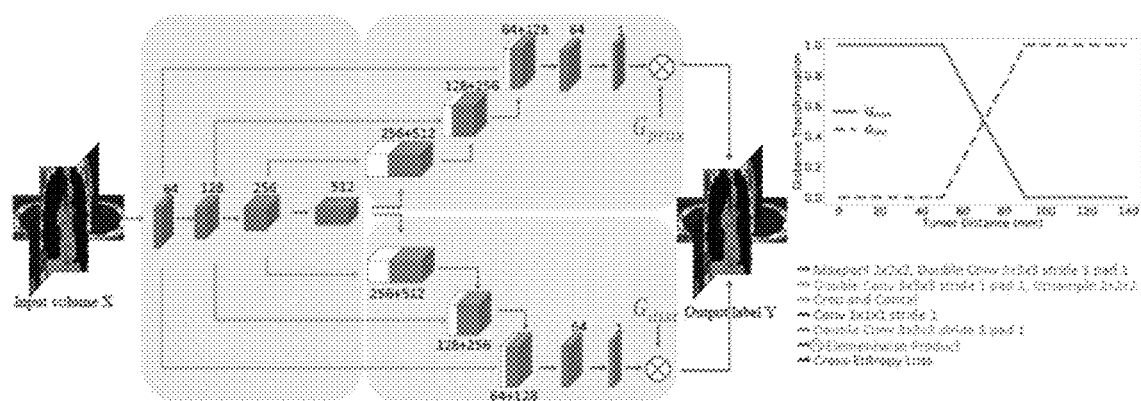
FIG. 8 illustrates an example of implementing the CAD method according to certain embodiments as shown in FIG. 4 and FIG. 7.

FIG. 8 illustrates an example of implementing the CAD method according to certain embodiments as shown in FIG. 4 and FIG. 7. As shown in FIG. 8, a to certain embodiments, underlying OSLN distributions may be divided into "tumor-proximal" and "tumor-distal" categories and solved accordingly. Specifically, a multi-branch network may adopt a shared encoder and two separate decoders to detect and segment the "tumor-proximal" and "tumor-distal" OSLN, respectively. A distance-based gating function may be designed to generate the corresponding OSLN sample weights for each branch. By applying the gating function at the outputs of decoders, each branch may be specialized to learn the "tumor-proximal" or "tumor-distal" OSLN features that emulates the physician's diagnosis process. Further, the process may leverage an early fusion (EF) of three modalities as input to the model, i.e., RTCT, PET, and 3D tumor distance map. RTCT depicts anatomical structures capturing the intensity, appearance, and contextual information, while PET provides metastasis functional activities. Meanwhile, the tumor distance map further encodes the critical distance information in the network. The fusion of these three modalities together can effectively boost the OSLN identification performance.

As shown in the framework illustrated in FIG. 8, according to certain embodiments, the CAD method may first compute the 3D tumor distance transformation map. Next, a multi-branch detection-by-segmentation network may be implemented where each branch focuses on one subgroup of OSLN segmentation. This is achieved by applying a binary or soft distance-gating function imposed on the penalty function at the output of the two branches. Hence, each branch can learn specific parameters to specialize in segmenting and detecting the tumor-proximal and tumor-adjacent OSLNs, respectively.

To stratify OSLNs into tumor-proximal and tumor-distal subgroups, the CAD method may first compute the 3D tumor distance transformation map, denoted as $X^D$, from the primary tumor O. The value at each voxel $x_i$ represents the shortest distance between this voxel and the mask of the primary tumor. Let B(O) be a set that includes the boundary voxels of the tumor. The distance transformation value at a voxel $x_i$ is computed as $$X^D(x_i) = \begin{cases} \min_{q \in B(O)} d(x_i, q) & \text{if } x_i \notin O \\ 0 & \text{if } x_i \in O \end{cases} \quad (3)$$

where $d(x_i, q)$ is the Euclidean distance from $x_i$ to $q$. $X^D$ can be efficiently computed using existing algorithms. Based on $X^D$, OSLNs may be divided into tumor-proximal and tumor-distal subgroups using either binary or soft distance-gating function.

OSLN identification may be implicitly associated with their distance distributions to the primary tumor in the diagnosis process of physicians. Hence, the CAD method may divide OSLN into tumor-proximal and tumor-distal subgroups and conduct detection accordingly. To do this, the CAD method may use a multi-branch detection-by-segmentation network with each branch focusing on segmenting one OSLN subgroup. Each branch is implemented by an independent decoder to learn and extract the subgroup-specific information, while they share a single encoder to extract the common OSLN image features. Assuming there are N data samples, the CAD method may denote a dataset as S={$(X_n^{CT}, X_n^{PET}, X_n^D, Y_n)\}_{n=1}^N$, where $X_n^{CT}$, $x_n^{PET}$, $x_n^D$ and $Y_n$ represent the non-contrast RTCT, registered PET, tumor distance transformation map, and ground truth OSLN segmentation mask, respectively. Without the loss of generality, n may be dropped for conciseness. The total number of branches may be denoted as M, where M=2 in certain embodiments. A convolutional neural network (CNN) segmentation model may be denoted as a mapping function E:P=f($\chi$; $\Theta$), where $\chi$ is a set of inputs, which consists of a single modality or a concatenation of multiple modalities. $\Theta$ indicates model parameters, and P means the predicted probability volume. Given that $p(y_i|x_i;\Theta_m)$ represents the predicted probability of a voxel $x_i \in \chi$ being the labeled class from the mth branch, the overall negative log-likelihood loss aggregated across M branches can be formulated as:

$$\mathcal{L} = \Sigma_m \mathcal{L}_m(\chi;\Theta_m,G_m) = -\Sigma_i \Sigma_m g_{m,i} \log(p(y_i|x_i;\Theta_m)) \quad (4)$$

where $G=\{G_m\}_{m=1}^M$ is introduced as a set of volumes containing the transformed gating weights at each voxel based on its distance to the primary tumor. At every voxel $x_i \in G$, the gating weights satisfy $\Sigma_m g_{m,i}=1$.

Based on the tumor distance map $X^D$, the gating functions may be designed to generate appropriate OSLN sample weights for different branches so that each branch specializes in learning the subgroup-specific features. In this case, the CAD method may explore two options: (1) binary distance gating and (2) soft distance gating.

Binary Distance Gating (BG). Based on the tumor distance map $X^D$, the CAD method may divide image voxels into two groups, $X_{prox}$ and $X_{dis}$, to be tumor-proximal and tumor-distal, respectively, where prox={$i | x_i^D \leq d_0, x_i^D \in X^D$} and dis={$i | x_i^D > d_0, x_i^D \in X^D$}. Therefore the gating transformations for two decoders are defined as $G_{prox}=1[x_i^D \leq d_0]$ and $G_{dist}=1-G_{prox}$, where 1[•] is an indicator function which equals 1 if its argument is true and 0 otherwise. In this way, the CAD method may divide the OSLNs strictly into two disjoint categories, and each branch focuses on decoding and learning from one category.

Soft Distance Gating (SG). The CAD method may further explore a soft gating method that linearly changes the penalty weights of OSLN samples as they are closer or further to the tumor. This can avoid a sudden change of weight values when samples are near the proximal and distal category boundaries. Recommended by a physician, the CAD method may formulate a soft gating module based on $X^D$ as following:

$$G_{prox}(x_i) = \begin{cases} 1 - \frac{x_i^D - d_{prox}}{d_{dist} - d_{prox}} & \text{if } d_{prox} < x_i^D \leq d_{dist} \\ 1 & \text{if } x_i^D \leq d_{prox}, \\ 0 & \text{if } x_i^D > d_{dist} \end{cases} \quad (5)$$

and $G_{dist}(x_i)=1-G_{prox}(x_i)$ accordingly.

To evaluate the CAD method as discussed above and illustrated in FIG. 4, FIG. 7, and FIG. 8, 141 non-contrast RTCTs of esophageal cancer patients, with all undergoing radiotherapy treatments. Radiation oncologists labeled 3D segmentation masks of the primary tumor and all OSLN. For each patient, a non-contrast RTCT and a pair of PET/CT scans are acquired. There is a total of 651 OSLN with voxel-wise annotations in the mediastinum or upper abdomen regions, as the largest annotated OSLN dataset to-date.

The patients are randomly split into 60%, 10%, 30% for training, validation, and testing, respectively.

In the implementation process, PET scan is registered to RTCT using the existing method. Then all coupling pairs of RTCT and registered PET images are resampled to have a consistent spatial resolution of 1×1×2.5 mm. To generate the 3D training samples, sub-volumes of 96×96×64 are cropped from the RTCT, registered PET, and the tumor distance map around each OSLN as well as randomly from the background. For the distance-gating related parameters, $d_0=7$ cm is chosen as the binary gating threshold, and $d_{prox}=5$ cm and $d_{dist}=9$ cm are chosen as the soft gating thresholds, respectively, as suggested by a clinician. Random rotations are further applied in the x-y plane within 10 degrees to augment the training data.

Detection-by-segmentation models are trained on two NVIDIA Quadra RTX 6000 GPUs with a batch size of 8 for 50 epochs. The RAdam optimizer with a learning rate of 0.0001 is used with a momentum of 0.9 and a weight decay of 0.0005. For inference, 3D sliding windows with a sub-volume of 96×96×64 and a stride of 64×64×32 voxels are processed. For each sub-volume, predictions from two decoders are weighted and aggregated according to the gating transformation Gm to obtain the final OSLN segmentation results.

For evaluation metrics, the hit, i.e., the correct detection, is used as criteria for the detection result. For an OSLN prediction, if it overlaps with any ground-truth OSLN, it is treated as a hit provided that its estimated radius is similar to the radius of the ground-truth OSLN within the range of [0.5, 1.5]. The performance is assessed using the mean and max recall (mRecall and $Recall_{max}$) at a precision range of [0.10, 0.50] with 0.05 interval, and the mean free-response operating characteristic (FROC) at 3, 4, 6, 8 FPs per patient. These operating points were chosen after confirming with the physician.

Using the binary and soft distance-based gating function, the multi-branch OSLN detection-by-segmentation method is denoted as multi-branch BG and multi-branch SG, respectively. They are compared against the following setups: (1) a single 3D UNet trained using RTCT alone or the early fusion (EF) of multi-modalities (denoted as single-net method); (2) Two separate UNets trained with the corresponding tumor-proximal and tumor-distal OSLN samples and results spatially fused together (denoted as multi-net BG); and (3) MULAN, a state-of-the-art (SOTA) general lesion detection method on DeepLesion that contains more than 10,000 enlarged LNs.

TABLE 4

Quantitative results of the provided methods with the comparison to other setups and the previous state-of-the-art

| Methods: | CT | EF | mRecall | $Recall_{max}$ | mFROC | FROC@4 | FROC@6 |
|---|---|---|---|---|---|---|---|
| single-net | ✓ | | 0.664 | 0.762 | 0.604 | 0.552 | 0.675 |
| single-net | | ✓ | 0.731 | 0.820 | 0.676 | 0.667 | 0.713 |
| multi-net BG | | ✓ | 0.747 | 0.825 | 0.695 | 0.668 | 0.739 |
| multi-branch BG | | ✓ | 0.761 | 0.845 | 0.679 | 0.667 | 0.716 |
| multi-branch SG | | ✓ | 0.782 | 0.843 | 0.724 | 0.729 | 0.738 |
| MULAN | ✓ | | 0.711 | 0.758 | 0.632 | 0.632 | 0.642 |
| MULAN | | ✓ | 0.725 | 0.781 | 0.708 | 0.718 | 0.720 |

The quantitative results and comparisons are given in Table 4. Several observations can be drawn on addressing the effectiveness of the methods provided by the present disclosure. (1) The multi-modality input, i.e., early fusion (EF) of RTCT, PET, and tumor distance map, are of great benefit for detecting the OSLN. There are drastic performance improvements of absolute 6.7% and 7.2% in mRecall and mFROC when EF is adopted as compared to using RTCT alone. These results validate that input channels of PET functional imaging and 3D tumor distance transform map are valuable for identifying OSLN. (2) The distance-based gating strategies are evidently effective as the options of multi-net BG, multi-branch BG, and multi-branch SG consistently increase the performance. For example, the multi-net BG model achieves 74.7% mRecall and 69.5% mFROC, which is a 1.6% and 1.9% improvement against the best single-net model (where no distance-based stratification is used). The performance further boosts with the network models of multi-branch BG and multi-branch SG, to the highest scores of 78.2% mRecall and 72.4% mFROC achieved by the multi-branch SG.

Using the distance-based gating strategy, the multi-branch methods proposed by the present disclosure perform considerably better than the multinet BG model. Even the second-best model multi-branch BG, the mean and maximal recalls have been improved by 1.4% (from 74.7% to 76.1%) and 2.0% (from 82.5% to 84.5%) against the multi-net BG model. When the multibranch framework is equipped with the soft-gating, marked improvements of absolute 3.5% and 2.9% in both mRecall and mFROC are observed as compared against to the multi-net BG model. This validates the effectiveness of the jointly trained multi-branch framework design, and the intuition that gradually changing OSLN weights for the proximal and distal branches are more natural and effective. As we recall, the multi-net baseline directly trains two separate 3D UNets targeted to segment each OSLN subgroup. Considering the limited OSLN training data (a few hundreds of patients), it can be overfitting prone from the split to even smaller patient subgroups.

Table 4 also compares with the SOTA universal lesion detection method, i.e., MULAN on DeepLesion. We have retrained the MULAN models using both CT and EF inputs, but even the best results, i.e., using EF, have a large gap (72.5% vs. 78.2% mRecall) with the distance-gating networks, which further proves that the tumor distance transformation cue plays a key role in OSLN identification.

Figure 9:
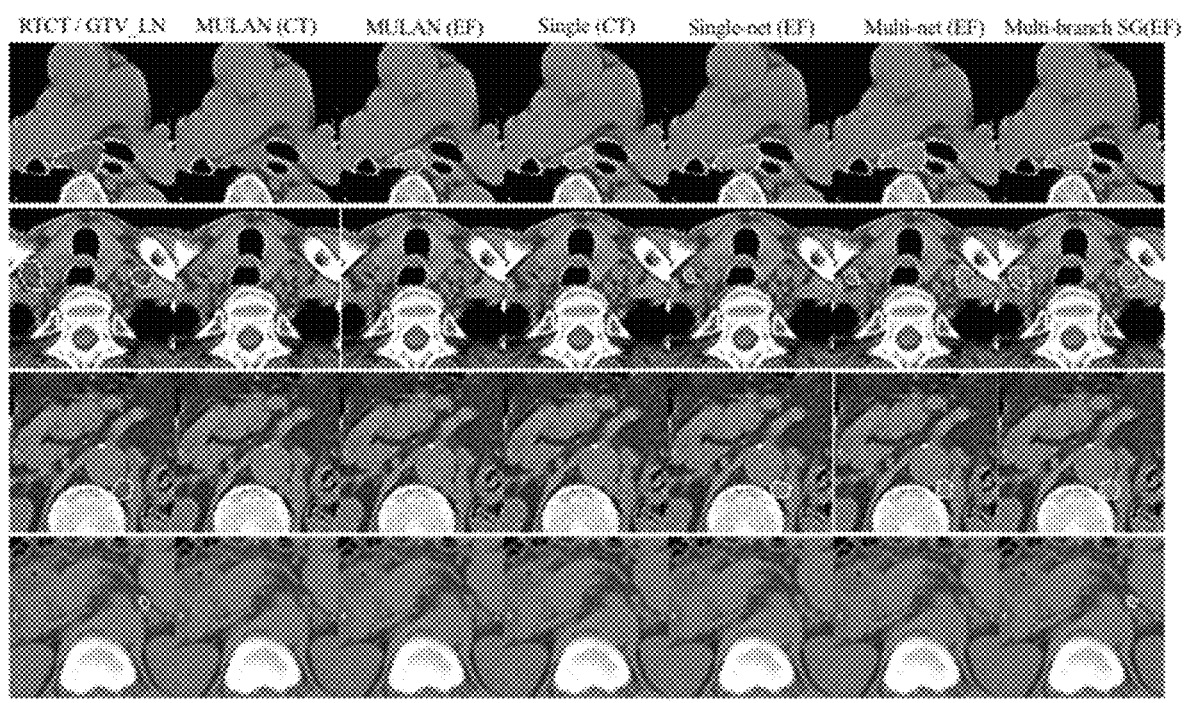
FIG. 9 illustrates examples of visualization results of the CAD method according to certain embodiments according to FIG. 4, FIG. 7, and FIG. 8.

FIG. 9 illustrates results of the CAD method according to FIG. 4, FIG. 7, and FIG. 8 compared to other baselines. Specifically, FIG. 9 shows four qualitative examples of detection results using different methods. The ground-truth OSLN overlaid on the RTCT images is shown by the while dashed-line contours in the first column of FIG. 9. The predicted segmentation masks are shown in the while dashed-line contours from the second column to the last column of FIG. 9. For an enlarged OSLN (as shown in the top row of FIG. 9), most methods can detect it correctly. However, as the size of OSLN becomes smaller and the contrast is poorer, the method provided by the present disclosure can still successfully detect them while other methods fail.

In summary, the CAD method and system provided by the present disclosure offer several contributions. First, the present disclosure addresses the clinically critical task of detecting, identifying and characterizing OSLNs. Further, the present disclosure provides a novel 3D distance stratification strategy to divide and conquer the complex distribution of OSLNs into tumor-proximal and tumor-distal classes, to be solved separately, which emulates the physician's decision process. Further, the present disclosure incorporates the PET imaging modality and 3D tumor distance maps into a two-stream detection-by-segmentation network. Further, the present disclosure provides a novel GLNet to incorporate high-level ontology-derived semantic attributes of OSLNs with localized features computed from RTCT/PET.

Further, according to certain embodiments, the provided CAD method imitates the physician's diagnosis process to tackle the problem of OSLN detection and segmentation. (1) A distance-based gating strategy is provided in a multi-task framework to divide the underlying OSLN distributions into "tumor-proximal" and "tumor-distal" categories and solve them accordingly. Specifically, a multi-branch network is provided to adopt a shared encoder and two separate decoders to detect and segment the "tumor-proximal" and "tumor-distal" OSLN, respectively. A distance-based gating function is designed to generate the corresponding OSLN sample weights for each branch. By applying the gating function at the outputs of decoders, each branch is specialized to learn the "tumor-proximal" or "tumor-distal" OSLN features that emulates the physician's diagnosis process. The CAD method also leverages the early fusion (EF) of three modalities as input to the model, i.e., RTCT, PET, and 3D tumor distance map. RTCT depicts anatomical structures capturing the intensity, appearance, and contextual information, while PET provides metastasis functional activities. Meanwhile, the tumor distance map further encodes the critical distance information in the network. The fusion of these three modalities together can effectively boost the OSLN identification performance. This approach is evaluated on a dataset comprising 651 voxel-wise labeled OSLN instances in 141 esophageal cancer patients, as the largest OSLN dataset to date for chest and abdominal radiotherapy. The provided CAD method significantly improves the detection mean recall from 72.5% to 78.2%, compared with the previous state-of-the-art lesion detection method. The highest achieved recall of 82.5% is also clinically relevant and valuable. As reported previously, human observers tend to have relatively low OSLN sensitivities, e.g., 80% by even very experienced radiation oncologists. This demonstrates the clinical values of the provided CAD method.

The method and apparatus provided in the present disclosure according to the embodiments are described in detail above. The principles and implementation manners provided in the present disclosure are described herein by using specific examples. The description of the above embodiments is only used to help understand the method provided in the present disclosure. At the same time, a person skilled in the art will make changes the specific embodiments and the application scope according to the idea provided in the present disclosure. In summary, the contents of the present specification should not be construed as limiting the present disclosure.

The present disclosure contains material that is subject to copyright protection. The copyright is the property of the copyright holder. The copyright holder has no objection to the reproduction of patent documents or patent disclosure in the official records and files of the Patent and Trademark Office.

What is claimed is:

1. A method for performing a computer-aided diagnosis (CAD), comprising:
acquiring a medical image set;
generating a three-dimensional (3D) tumor distance map corresponding to the medical image set, each voxel of the tumor distance map representing a distance from the voxel to a nearest boundary of a primary tumor present in the medical image set; and
performing neural-network processing of the medical image set to generate a predicted probability map to predict presence and locations of oncology significant lymph nodes (OSLNs) in the medical image set, wherein voxels in the medical image set are stratified and processed according to the tumor distance map, wherein:
the medical image set includes a 3D non-contrast computer tomography (CT) image and a 3D positron emission tomography (PET) image registered to the CT image; and
performing neural-network processing of the medical image set includes:
dividing voxels in each of the CT image and the PET image into tumor-proximal voxels and tumor-distal voxels according to the tumor distance map and a distance threshold;
processing the CT image with a first sub-network trained on CT images with corresponding ground-truth maps to generate a first prediction map based on the tumor-proximal voxels and a second prediction map based on the tumor-distal voxels;
processing the CT image, the PET image, and the tumor distance map with a second sub-network jointly trained on CT images, PET images, tumor distance maps, and corresponding ground-truth maps to generate a third prediction map based on the tumor-proximal voxels and a fourth prediction map based on the tumor-distal voxels; and
performing a fusion operation on the first, second, third and fourth prediction maps to generate a fused prediction map.

2. The method according to claim 1, wherein the fusion operation includes:
performing an element-wise maximum operation on the first and third prediction maps to generate a fifth prediction map;
performing an element-wise maximum operation on the second and fourth prediction maps to generate a sixth prediction map; and
performing a union operation on the fifth and sixth prediction maps to generate the fused prediction map.

3. The method according to claim 2, wherein performing neural-network processing of the medical data set further includes:
applying a second-stage neural-network processing on the fused prediction map to generate the predicted probability map.

4. The method according to claim 3, wherein applying the second-stage neural-network processing on the fused prediction map includes:
applying a threshold to the fused prediction map to generate a binary prediction map;
based on the binary prediction map, generating OSLN candidates, each OSLN candidate corresponding to an image patch of the binary prediction map;
for each OSLN candidate:
processing the corresponding image patch with a local feature extractor to generate a first feature vector corresponding to local features of the OSLN candidate;
processing the OSLN candidate with a global feature extractor to generate a second feature vector corresponding to complementary features that distinguish true OSLNs from false ones;
concatenating the first feature vector with the second feature vector to generate a combined feature vector; and
passing the combined feature vector through a fully connected neural-network (CNN) layer to generate a final OSLN classification score for the OSLN candidate.

5. The method according to claim 4, wherein the local feature extractor includes a multi-scale 3D CNN with a 3D region of interest (ROI)-global average pulling (GAP) layer.

6. The method according to claim 4, wherein the global feature extractor includes a lesion tagging module pre-trained on radiology reports including a variety of tissue types.

7. A non-transitory computer-readable storage medium storing a plurality of instructions, wherein when being executed by a processor, the plurality of instructions cause the processor to perform the method for computer-aided diagnosis (CAD) according to claim 1.

8. The non-transitory computer-readable storage medium according to claim 7, wherein when the plurality of instructions are executed by a processor, the processor is further caused to:
perform an element-wise maximum operation on the first and third prediction maps to generate a fifth prediction map;
perform an element-wise maximum operation on the second and fourth prediction maps to generate a sixth prediction map; and
perform a union operation on the fifth and sixth prediction maps to generate the fused prediction map.

9. A method for performing a computer-aided diagnosis (CAD), comprising:
acquiring a medical image set;
generating a three-dimensional (3D) tumor distance map corresponding to the medical image set, each voxel of the tumor distance map representing a distance from the voxel to a nearest boundary of a primary tumor present in the medical image set; and
performing neural-network processing of the medical image set to generate a predicted probability map to predict presence and locations of oncology significant lymph nodes (OSLNs) in the medical image set, wherein voxels in the medical image set are stratified and processed according to the tumor distance map, wherein performing neural-network processing of the medical image set includes:
processing the medical image set with a detection network containing a single encoder followed by a plurality of decoder branches, wherein the single encoder is trained to extract common OSLN features, and each decoder branch is trained to extract and output a subgroup of OSLN features;
applying a plurality of distance-based gating functions to outputs of the plurality of decoder branches to generate a plurality of subgroups of distance-gated OSLN features, wherein each distance-based gating function applies tumor-distance dependent OSLN sample weights to the output of a corresponding decoder branch according to the tumor distance map to generate one subgroup of distance-gated OSLN features; and
fusing the plurality of subgroups of distance-gated OSLN features to form the predicted probability map.

10. The method according to claim 9, wherein:
the medical image set includes a 3D non-contrast CT image and a 3D PET image registered to the CT image; and
performing neural-network processing of the medical image set includes an early fusion of the CT image, the PET image, and the tumor distance map.

11. The method according to claim 9, wherein:
the detection network contains two decoder branches including a first decoder branch and a second decoder branch; and
the distance-based gating functions include a first binary distance gating function configured to pass tumor-proximal features and a second binary distance gating function configured to pass tumor-distal features.

12. The method according to claim 9, wherein:
the distance-based gating functions are soft gating functions having OSLN sample weights linearly dependent on distances to the primary tumor.

13. A device for performing computer-aided diagnosis (CAD), comprising:
a memory, storing computer-executable instructions; and
a processor, coupled with the memory and, when the computer-executable instructions being executed, configured to perform the method for performing computer-aided diagnosis (CAD) according to claim 9.

14. A non-transitory computer-readable storage medium containing a plurality of instructions, wherein when being executed by a processor, the plurality of instructions cause the processor to perform the method for computer-aided diagnosis (CAD) according to claim 9.

15. A device for performing computer-aided diagnosis (CAD), comprising:
a memory, storing computer-executable instructions; and
a processor, coupled with the memory and, when the computer-executable instructions being executed, configured to:
acquire a medical image set;
generate a three-dimensional (3D) tumor distance map corresponding to the medical image set, each voxel of the tumor distance map representing a distance from the voxel to a nearest boundary of a primary tumor present in the medical image set; and
perform neural-network processing of the medical image set to generate a predicted probability map to predict presence and locations of oncology significant lymph nodes (OSLNs) in the medical image set, wherein voxels in the medical image set are stratified and processed according to the tumor distance map, wherein:
the medical image set includes a 3D non-contrast computer tomography (CT) image and a 3D positron emission tomography (PET) image registered to the CT image; and
the processor is further configured to:
divide voxels in each of the CT image and the PET image into tumor-proximal voxels and tumor-distal voxels according to the tumor distance map and a distance threshold;
process the CT image with a first sub-network trained on CT images with corresponding ground-truth maps to generate a first prediction map based on the tumor-proximal voxels and a second prediction map based on the tumor-distal voxels;
process the CT image, the PET image, and the tumor distance map with a second sub-network jointly trained on CT images, PET images, tumor distance maps, and corresponding ground-truth maps to generate a third prediction map based on the tumor-proximal voxels and a fourth prediction map based on the tumor-distal voxels; and perform a fusion operation on the first, second, third and fourth prediction maps to generate a fused prediction map.

16. The device according to claim 15, wherein the processor is further configured to:

perform an element-wise maximum operation on the first and third prediction maps to generate a fifth prediction map;

perform an element-wise maximum operation on the second and fourth prediction maps to generate a sixth prediction map; and perform a union operation on the fifth and sixth prediction maps to generate the fused prediction map.

17. The device according to claim 16, wherein the processor is further configured to:

apply a second-stage neural-network processing on the fused prediction map to generate the predicted probability map.

18. The device according to claim 17, wherein the processor is further configured to:

apply a threshold to the fused prediction map to generate a binary prediction map;

based on the binary prediction map, generate OSLN candidates, each OSLN candidate corresponding to an image patch of the binary prediction map;

for each OSLN candidate:

process the corresponding image patch with a local feature extractor to generate a first feature vector corresponding to local features of the OSLN candidate;

process the OSLN candidate with a global feature extractor to generate a second feature vector corresponding to complementary features that distinguish true OSLNs from false ones;

concatenate the first feature vector with the second feature vector to generate a combined feature vector; and pass the combined feature vector through a fully connected neural-network (CNN) layer to generate a final OSLN classification score for the OSLN candidate.

19. The device according to claim 18, wherein the local feature extractor includes a multi-scale 3D CNN with a 3D region of interest (ROI)-global average pulling (GAP) layer.

20. The device according to claim 18, wherein the global feature extractor includes a lesion tagging module pre-trained on radiology reports including a variety of tissue types.

* * * * *